US009365877B2

(12) United States Patent
Fremy et al.

(10) Patent No.: US 9,365,877 B2
(45) Date of Patent: Jun. 14, 2016

(54) PREPARATION OF PROCESS OF L-METHIONINE

(75) Inventors: Georges Fremy, Sauveterre de Bearn (FR); Patrice Barre, Lons (FR); So Young Kim, Gyeonggi-do (KR); Sung Kwang Son, Seoul (KR); Sang Mok Lee, Seoul (KR)

(73) Assignees: CJ CHEILJEDANG CORPORATION, Seoul (KR); ARKEMA FRANCE, Colombes (FR)

( * ) Notice: Subject to any disclaimer, the term of this patent is extended or adjusted under 35 U.S.C. 154(b) by 0 days.

(21) Appl. No.: 14/342,582

(22) PCT Filed: Sep. 2, 2011

(86) PCT No.: PCT/EP2011/065241
§ 371 (c)(1),
(2), (4) Date: Mar. 4, 2014

(87) PCT Pub. No.: WO2013/029690
PCT Pub. Date: Mar. 7, 2013

(65) Prior Publication Data
US 2014/0227746 A1    Aug. 14, 2014

(51) Int. Cl.
*C12P 13/12* (2006.01)
*C12P 13/04* (2006.01)

(52) U.S. Cl.
CPC ..................................... *C12P 13/12* (2013.01)

(58) Field of Classification Search
CPC ....................................................... C12P 13/12
USPC .................................................. 435/113, 106
See application file for complete search history.

(56) References Cited

U.S. PATENT DOCUMENTS

| 6,320,076 | B1 * | 11/2001 | Hsu et al. ...................... 562/581 |
| 8,609,396 | B2 | 12/2013 | Kim et al. |
| 2011/0053252 | A1 | 3/2011 | Kim et al. |
| 2012/0123158 | A1 * | 5/2012 | Kim et al. ...................... 562/559 |
| 2013/0273614 | A1 | 10/2013 | Kim et al. |

FOREIGN PATENT DOCUMENTS

| EP | 2292783 A2 | 3/2011 |
| FR | 2851255 A1 | 8/2004 |
| FR | 2851256 A1 | 8/2004 |
| WO | 9317112 A1 | 9/1993 |
| WO | 2008013432 A1 | 1/2008 |
| WO | 2012087038 A2 | 6/2012 |

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Kisselev L., Polypeptide release factors in prokaryotes and eukaryotes: same function, different structure. Structure, 2002, vol. 10: 8-9.*
Seffernick et al., Melamine deaminase and Atrazine chlorohydrolase: 98 percent identical but functionally different. J. Bacteriol., 2001, vol. 183 (8): 2405-2410.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Witkowski et al., Conversion of b-ketoacyl synthase to a Malonyl Decarboxylase by replacement of the active cysteine with glutamine. Biochemistry, 1999, vol. 38: 11643-11650.*
International Search Report for PCT/EP2011/065241 dated Mar. 2, 2012.
Yeom, H-J. et al, "Regulation of Enzymes Involved in Methionine Biosynthesis in *Corynebacterium glutamicum*," Journal of Microbiology and Biotechnology, 2004, vol. 14, No. 2, pp. 373-378.
Database WPI, Week201062, Thomson Scientific, London, GB, AN2010-K90589 & WO2010/098629, 2010.
English Abstract of FR2851255, Publication Date: Aug. 20, 2004.
English Abstract of FR2851256, Publication Date: Aug. 20, 2004.

* cited by examiner

*Primary Examiner* — Ganapathirama Raghu
(74) *Attorney, Agent, or Firm* — Millen White Zelano and Branigan, PC; John Sopp; Anthony Zelano

(57) ABSTRACT

The present invention relates to a method for producing L-methionine using a bio-synthesis process and a specific enzymatic process. More particularly, the present invention relates to a method for producing L-methionine with high yield by enzyme conversion reaction from L-methionine precursor in the presence of methyl mercaptan ($CH_3SH$). The process of the present invention enables selective production of L-methionine which may be used in various fields of industry, such as feed- and food-additives, as raw material for medical supplies, pharmaceutical drugs, and the like.

18 Claims, No Drawings

PREPARATION OF PROCESS OF L-METHIONINE

The present invention relates to a method for producing L-methionine using a bio-synthesis process and a specific enzymatic process. More particularly, the present invention relates to a method for producing L-methionine with high yield by enzyme conversion reaction from L-methionine precursor in the presence of methyl mercaptan ($CH_3SH$). The process of the present invention to produce L-methionine is more environmental-friendly than the conventional methods known from the prior art, and enables selective production of L-methionine which may be used in various fields of industry, such as feed- and food-additives, as raw material for medical supplies, pharmaceutical drugs, and the like.

Methionine is one of the essential amino acids of the human body and has been widely used as feed and food additives and further used as a synthetic raw material for medical solutions, medical supplies, as well as for pharmaceutical drugs. Methionine acts as a precursor of such compounds as choline (lecithin) and creatine and at the same time is used as a synthetic raw material for cysteine and taurine. Methionine can also provide sulfur.

S-Adenosyl-L-methionine is derived from L-methionine and plays a certain role in providing methyl group in human body and also is involved in the synthesis of various neurotransmitters in the brain. L-Methionine (L-Met) and/or S-adenosyl-L-methionine (SAM) inhibits fat accumulation in the liver and artery promoting lipid metabolism. It also improves blood circulation in the brain, heart and kidney and thus is used as an anti-depression agent for alleviating inflammation, muscle pain, and liver disease, particularly is effective in the liver disease caused by alcohol.

It may also be used for promoting digestion, detoxication and excretion of toxic substances and excretion of heavy metals such as lead. It has anti-inflammatory effect on bone and joint diseases and promotes joint-recovery, and also as an essential nutrient for hair, thereby preventing hair loss.

Methionine is already known to be prepared according to chemically and/or biologically syntheses, which have been the subject of a number of works and studies, mainly aiming at proposing more efficient, more selective, and more environmental friendly preparation methods.

In the chemical synthesis, methionine is mostly produced by hydrolysis of 5-(β-methylmercaptoethyl)hydantoin. The chemically synthesized methionine has a disadvantage of only being produced as a mixed form of L-type and D-type.

In the biological synthesis, methionine is produced by method using proteins involved in methionine synthesis. L-Methionine is biosynthesized from homoserine by the action of the enzyme expressed by various genes such as metA, metB, metC, metE and metH. Particularly, metA is the gene encoding homoserine-O-succinyl transferase which is the first enzyme necessary for methionine biosynthesis, and it converts homoserine into O-succinyl-L-homoserine. O-Succinylhomoserine lyase or cystathionine-γ-synthase coded by metB gene converts O-succinyl-L-homoserine into cystathionine.

Cystathionine-β-lyase coded by metC gene converts cystathionine into L-homocysteine. MetE encodes cobalamine-independent methionine synthase and metH encodes cobalamine-dependent methionine synthase, both of which convert L-homocysteine into L-methionine. At this time, 5,10-methylenetetrahydrofolate reductase coded by metF and serine hydroxymethytransferase coded by glyA work together to synthesize N(5)-methyltetrahydrofolate providing methyl group necessary for L-methionine synthesis. L-Methionine is synthesized by a series of organic reactions by the above enzymes.

The methionine produced by the conventional biological method is of L-type, which has advantages but the production amount is too small. This is because the methionine biosynthetic pathway has very tight feed-back regulation systems. Once methionine is synthesized to a certain level, the final product methionine inhibits the transcription of metA gene encoding the primary protein for initiation of methionine biosynthesis. Over-expression of metA gene itself cannot increase methionine production because the metA gene is suppressed by methionine in the transcription stage and then degraded by the intracellular proteases in the translation stage.

The conventional methionine biosynthesis method uses cystathionine synthase metabolism pathway to produce methionine, so the enzyme reaction process is inefficient due to the sulfide toxicity and by-products generation. In addition, feed-back regulation in methionine synthesis pathway inhibits its mass-production of methionine.

An alternative method of producing L-methionine to overcome the above problems is disclosed in the international application published under no. WO 2008/013432. This alternative method is composed of two-step process in which L-methionine precursor is produced by fermentation and L-methionine precursor is selectively converted to L-methionine by enzymes.

More precisely WO 2008/013432 discloses a method for producing L-methionine comprising the steps of 1) preparing L-methionine precursor producing strain and producing L-methionine precursor by the fermentation of the strain, and 2) producing L-methionine and organic acid by the enzyme reaction with the L-methionine precursor.

Step 2) process includes the process for producing L-methionine and organic acid by enzyme reaction using an enzyme having the activity of cystathionine synthase or O-succinyl homoserine sulfydrylase or O-acetyl homoserine sulfhydrylase or the strain containing these enzyme activities by using O-succinyl homoserine or O-acetyl homoserine produced from the above L-methionine precursor producing strain, and methyl mercaptan as a substrate.

WO 2008/013432 provides general information on step 2) which consists in converting an L-methionine precursor to L-methionine by the enzyme reaction in the presence of methyl mercaptan.

Even though the overall yield in L-methionine is satisfying, there still exists a need for even more improving the bio-synthesis of L-methionine, particularly for improving the step of enzymatic conversion of the L-methionine precursor with methyl mercaptan to specifically obtain L-methionine with improved yields.

Therefore, a first object of the present invention is to provide an improved process for the enzymatic conversion of an L-methionine precursor with methyl mercaptan to obtain L-methionine with improved yields.

More particularly, the present invention provides the method for producing L-methionine by enzyme reaction of an L-methionine precursor and methyl mercaptan.

In the process of the present invention, the L-methionine precursor may be any precursor known in the art and which is able to be converted into L-methionine by enzyme reaction with methyl mercaptan, and for example such as disclosed in WO 2008/013432. According to a preferred aspect of the present invention, the enzyme used for converting the L-methionine precursor is preferably chosen from among cystathionine synthase or O-succinyl homoserine sulfhydrylase or O-acetyl homoserine sulfydrylase by using homoserine, O-phospho-homoserine, O-succinyl homoserine or O-acetyl homoserine accumulated as a substrate.

More preferably, the L-methionine precursor to be used in the process of the invention is chosen from O-succinyl homoserine (OSH) and O-acetyl homoserine (OAH). Still more preferably, the L-methionine precursor is OAH.

In process of the invention, where O-acetyl homoserine is used as L-methionine precursor, preferably cystathionine-γ-synthase or O-succinyl homoserine sulfhydrylase or O-acetyl homoserine sulfhydrylase (OAHS) derived from *Leptospira* sp., *Chromobacterium* sp., or *Hyphomonas* sp., more preferably derived from *Leptospira meyeri, Pseudomonas aurogenosa, Hyphomonas Neptunium* or *Chromobacterium Violaceum*, can be used.

The enzyme reaction process of the present invention may be represented with the following schemes:

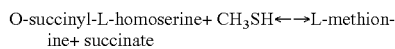

O-succinyl-L-homoserine+ CH₃SH←→L-methionine+ succinate

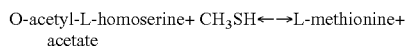

O-acetyl-L-homoserine+ CH₃SH←→L-methionine+ acetate wherein the reaction is an enzymatic reaction and is operated with a specific pressure range of methyl mercaptan (CH₃SH).

In the above reactions, the CH₃S— residue of methyl mercaptan is substituted with the succinate or acetate residue of O-succinyl homoserine or of O-acetyl homoserine to produce L-methionine. According to the invention, methyl mercaptan is added at a precise pressure range, as further explained in the present description.

The above described reaction of conversion of the L-methionine precursor to L-methionine in the presence of methyl mercaptan is an enzymatic reaction, as disclosed for example in WO 2008/013432.

WO 2008/013432 provides details on the nature and preparation of the enzymes that may be used, and are enzymes having the suitable activity of converting an L-methionine precursor to L-methionine in the presence of methyl mercaptan. Such appropriate enzymes may for example be prepared using expression of genes according to biotechnological processes.

As non limiting examples, the sequence of the genes encoding the enzymes having the above enzyme activity can be obtained from the database of NCBI, USA, and DNA data bank (KEGG), Japan.

For the biological conversion reaction, a gene is cloned from the obtained gene sequence, which is then introduced into an expression vector. The enzyme is expressed in active form from a recombinant strain. Both the enzyme expressing strain and the expressed enzyme can be directly used for the reaction.

The enzymes expressed from above genes or the microbial strains expressing those enzymes can be directly mixed, partly or not, with the fermentation supernatant or the fermentation broth accumulated with L-methionine precursor to start the reaction. In a preferred embodiment of the invention, O-succinyl homoserine or O-acetyl homoserine accumulated in the fermentation solution can be converted into the L-methionine by cystathionine -γ-synthase or O-acetyl homoserine sulfhydrylase or O-succinyl homoserine sulfhydrylase derived from *Pseudomonas* sp., *Chromobacterium* sp., *Leptospira* sp. or *Hyphomonas* sp.

More preferably, O-succinyl homoserine accumulated in the fermentation solution is converted into methionine by cystathionine-γ-synthase or O-acetyl homoserine sulfhydrylase or O-succinyl homoserine sulfhydrylase derived from *Pseudomonas aurogenosa, Pseudomonas putida* or *Chromobacterium Violaceum*. O-Acetyl homoserine accumulated in the fermentation solution is converted into methionine by cystathionine-γ-synthase or O-acetyl homoserine sulfhydrylase or O-succinyl homoserine sulfhydrylase derived from *Leptospira meyeri, Hyphomonas Neptunium* or *Chromobacterium Violaceum*.

Each gene is expressed in pCL-CJI vector (CJ, Korea), the expression vector for *E. coli*, and the expressed protein is obtained from enzyme solution prepared by cell lysis using sonication. The enzyme solution is added to the fermentation solution accumulated O-succinyl homoserine or O-acetyl homoserine, and methyl mercaptan is also added thereto to start the reaction.

The reaction is confirmed using DTNB [5,5-dithiobis(2-nitro-benzoic acid, Sigma, USA] and the reaction product is analyzed by HPLC. In the present invention, by-products such as succinic acid or acetic acid can be additionally obtained, without a separate production process, by the reaction of methyl mercaptan with O-succinyl homoserine and O-acetyl homoserine respectively.

The enzymatic reaction of the L-methionine precursor with CH₃SH may be illustrated by the following scheme:

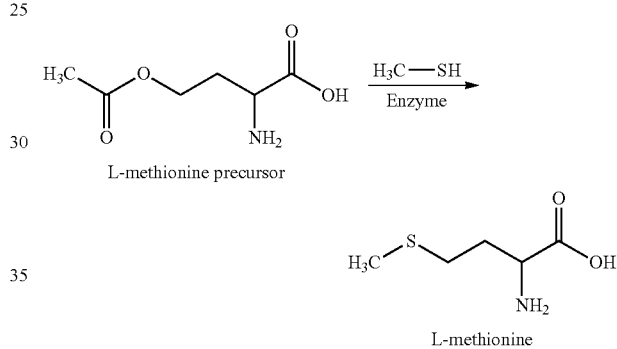

As described hereinbefore, the enzymatic conversion of the precursor of L-methionine is carried out in the presence of methyl mercaptan, (CH₃SH) and, according to the present invention, under CH₃SH pressure, more specifically so that the CH₃SH partial pressure above the reaction medium is within as specific pressure range.

The process depicted in WO 2008/013432 does not provide for detailed operating conditions regarding this enzymatic conversion of the L-methionine precursor to L-methionine in the presence of methyl mercaptan, particularly methyl mercaptan is used without any indication on its way of administration. There is also no information of the conversion rate of the L-methionine precursor.

The present inventors have now discovered that the conversion rate of the L-methionine precursor greatly depends on the way of administration of methyl mercaptan to the reaction medium and particularly to the CH₃SH partial pressure present in the conversion reaction vessel used for this reaction.

More precisely, it clearly appears that there is a thin window, from 0 to the CH₃SH saturated vapour pressure at the reaction temperature, in which the conversion rate shifts from a beneficial to a strong inhibiting effect of the pressure.

There is therefore an optimum CH₃SH partial pressure range where conversion of the methionine precursor (e.g. OAHS) into methionine is maximal. It would have been expected that the higher the CH₃SH pressure, the greater the amount of solubilised CH₃SH, consequently the faster the kinetics of the conversion reaction and therefore the higher the conversion into methionine.

However it has been observed that, still increasing the $CH_3SH$ pressure is detrimental to the said conversion. Without being bound to theory, one explanation to this phenomenon could be that a too important $CH_3SH$ pressure leads to a too high amount of $CH_3SH$ present in the reaction medium. This excessive amount of $CH_3SH$ would block the active sites of the enzyme, and lead to an inhibition of the reaction. There would therefore exist a competition between the reaction kinetics and the access to the reactive sites of the enzyme.

According to the process of the present invention, the optimal $CH_3SH$ partial pressure in the reaction vessel over the reaction medium ranges from 10 kPA to 180 kPA, preferably from 51 kPa to 180 kPa, more preferably from 51 kPa to 160 kPa, still more preferably from about 80 kPa to about 160 kPa, advantageously from about 90 kPa to about 150 kPa, for example the $CH_3SH$ partial pressure is about 100 kPa to 150 kPa, at the reaction temperature.

These specific conditions allow for a fast kinetics of conversion as well as a high L-methionine precursor conversion rate, for example a 100% conversion rate could be obtained after a 2 hours reaction time.

The reaction is generally carried out at an appropriate temperature which is adapted for enzymatic conversion of a L-methionine precursor to L-methionine, for example as disclosed in WO 2008/013432. Advantageously, the reaction temperature ranges from 20° C. to 45° C., preferably from 25° C. to 40° C., still more preferably from 30° C. to 40° C.

More precisely, methyl mercaptan is introduced into the reactor via a dip-tube, into the reaction medium. Methyl mercaptan is introduced by applying a nitrogen pressure on an outside methyl mercaptan vessel. The methyl mercaptan flow rate is controlled by varying the nitrogen pressure, and with exhaust valves. A portion of the introduced methyl mercaptan is dissolved in the reaction medium, whereas the remaining portion is in gaseous form over the reaction medium.

Solubility of methyl mercaptan in the reaction may be increased by mixing methyl mercaptan with dimethyl sulfide (DMS) at an appropriate ratio. Use of DMS improves the transformation rate of L-methionine and organic acids from the precursor of L-methionine, as well as the yield of L-methionine production.

Preferably, when DMS is mixed with methyl mercaptan, the molar ratio of methyl mercaptan/DMS ranges from 1:0.05 to 1:1, more preferably from 1:0.20 to 1:1, still more preferably from 1:0.25 to about 1:0.50. By way of example, DMS may be mixed at a ratio of about 5% to 25%, preferably 20% to 25% relative to the total of methyl mercaptan and DMS.

After introduction of the required amount of methyl mercaptan into the reactor, and an equilibrium state between the liquid phase and the gaseous phase is reached, methyl mercaptan can be added or removed, the partial pressure over the reaction medium being checked by any known manner, e.g. a manometer. The methyl mercaptan partial pressure is controlled all along the reaction until completeness.

According to a preferred embodiment, the introduction of methyl mercaptan is stopped when the stoichiometric amount is introduced, and from this point, the methyl mercaptan partial pressure decreases until completion of the reaction.

As the enzymatic conversion reaction of the reaction also leads to an acidic by-product, the pH of the reaction may advantageously be controlled and maintained at about a neutral or slightly acid value, preferably the pH of the reaction medium is maintained between 6 and 7 all along the conversion.

In order to adjust the pH value between 6 and 7, one or more basic compound may be added to the reaction medium, said basic compound being an aqueous base, as disclosed in WO 2008/013432, for example chosen from among ammonium hydroxide, potassium hydroxide, ammonia, and the like, for example an ammonia aqueous solution.

The conversion reaction is also advantageously conducted in the presence of a co-enzyme, according to known techniques in the art, for example as disclosed in WO 2008/013432. An example of such co-enzyme is pyridoxal-5'-phosphate (PLP).

While carrying out the process of the present invention, setting the $CH_3SH$ partial pressure to the as above defined preferred values, the conversion rate of the L-methionine precursor is at least 10% to 20% higher, than when the $CH_3SH$ partial pressure is outside the ranges of the process of the invention. Under these specific conditions, it could also be observed that the L-methionine precursor conversion rate may be greater than 80% as early as after 0.5 hour, and even equal to 100% after 2 hours reaction time.

This particularly fast complete conversion rate results in an overall preparation of L-methionine, wherein the enzymatic conversion of the L-methionine precursor is not a limiting step, and thereby allows for an overall bio-synthesis of L-methionine with high yields, greater than those known so far in the prior art.

Accordingly, a second aspect of the present invention relates to a process for the preparation of L-methionine comprising the steps of:
1) preparing a L-methionine precursor-producing strain and producing a L-methionine precursor by the fermentation of the strain,
2) converting said L-methionine precursor into L-methionine, by enzyme reaction in the presence of $CH_3SH$ at a partial pressure ranging from 10 kPa to 180 kPa, preferably from 50 kPa to 160 kPa, more preferably from about 80 kPa to about 150 kPa, and
3) collecting the obtained L-methionine.

This overall process of bio-synthetic preparation of L-methionine may be represented by the following scheme:

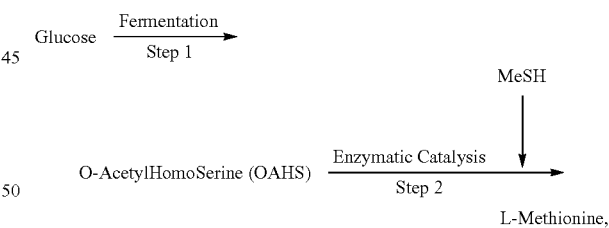

wherein the L-methionine precursor is OAHS, prepared via gene expression, from the fermentation of glucose.

The fermentation process of step 1 may be any fermentation process known in the art, and for example as disclosed in WO 2008/013432.

Particularly, in step 1) of the process, a L-methionine precursor producing strain is generated and fermented for the accumulation of L-methionine precursor in the culture media.

The L-methionine precursor of the present invention is preferably O-acetyl homoserine or O-succinyl homoserine. The "L-methionine precursor-producing strain" as used herein refers to a prokaryotic or eukaryotic microorganism strain that is able to accumulate L-methionine precursor by the manipulation according to the present invention.

For example, the strain can be selected from the group consisting of *Escherichia* sp., *Erwinia* sp., *Serratia* sp., *Providencia* sp., *Coryne* bacteria sp., *Pseudomonas* sp., *Leptospira* sp., *Salmonellar* sp., *Brevibacteria* sp., *Hypomononas* sp., *Chromobacterium* sp. and *Norcardia* sp. microorganisms or fungi or yeasts.

Preferably, the microorganisms of *Pseudomonas* sp., *Norcardia* sp. and *Escherichia* sp. can be used to produce O-succinyl homoserine, and the microorganisms of *Escherichia* sp., *Corynebacterium* sp., *Reptospira* sp. and yeasts can be used to produce O-acetyl homoserine. More preferably, the microorganisms of *Escherichia* sp. can be used, and most preferably *Escherichia coli* (hereinafter referred to as "*E. coli*) can be used. In addition, the foreign genes can be introduced into the *Escherichia* sp. microorganism to selectively produce O-succinyl homoserine and O-acetyl homoserine.

The L-methionine precursor producing strain can be prepared from the strain producing L-lysine, L-threonine or L-isoleucine. Preferably, it can be prepared by using the L-threonine producing strain. With this strain, homoserine synthesis is already higher and the production of methionine precursor can be resultantly increased.

So, methionine precursor can be accumulated by deleting or weakening a gene involved in threonine biosynthesis pathway and then metA or metY or MetZ gene, using the L-threonine producing strain. It is more preferred to delete or weaken thrB gene first and then metB, metY or metZ to synthesize methionine precursor. In the meantime, the enhancement of metA or metX gene expression results in the increase of methionine precursor synthesis.

As described herein before, the "L-threonine-producing strain" of the invention refers to a prokaryotic or eukaryotic microorganism strain that is able to produce L-threonine in vivo. For example, the strain can be include L-threonine producing microorganism strains belongs to *Escherichia* sp., *Erwinia* sp., *Serratia* sp., *Providencia* sp., *Corynebacterium* sp. and *Brevibacterium* sp. Among these, *Escherichia* sp. microorganism is preferred and *Escherichia coli* is more preferred.

The L-threonine producing strain includes not only the microorganisms in nature but also their mutants which are exemplified by microorganisms that has a leaky requirement for iso-leucine and is resistant to L-lysine analogues and α-aminobutyric acid; and is mutated by additionally introducing at least an extra copy of endogenous phosphoenol pyruvate carboxylase (ppc) gene; and is inactivated pckA gene involved in the conversion process of oxaloacetate (OAA) that is an intermediate of L-methionine synthesis into phosphoenol pyruvate (PEP); and is inactivated tyrR gene inhibiting the expression of tyrB gene involved in L-methionine biosynthesis; and is inactivated galR gene inhibiting the expression of galP gene involved in glucose transport.

The L-lysine analogues herein may be one or more compounds selected from the group consisting of S-(2-aminoethyl)-L-cysteine and δ-methyl-L-lysine. In a preferred embodiment of the present invention, CJM002, the L-threonine producing and L-methionine-independent strain mutated from TF4076 (KFCC 10718, Korean Patent No. 92-8365), the L-threonine producing *E. coli* mutant strain, was used. TF4076 has a requirement for methionine, and is resistant to methionine analogues (ex, α-amino-β-hydroxy valeric acid, AHV), lysine analogues (ex, S-(2-aminoethyl)-L-cysteine, AEC), and isoleucine analogues (ex. α-aminobutyric acid).

The culture of the L-methionine precursor producing strain prepared above can be performed by a proper medium and conditions known to those in the art. It is well understood by those in the art that the culture method can be used by easily adjusting, according to the selected strain. For example, the culture method including, but not limited to batch, continuous culture and fed-batch. A variety of culture methods are described for example in "*Biochemical Engineering*" by J. M. Lee, Prentice-Hall International Editions, pp 138-176.

The medium has to meet the culture conditions for a specific strain. A variety of microorganism culture mediums are described for example in "*Manual of Methods for General Bacteriology*" by the American Society for Bacteriology, Washington D.C., USA, 1981. Those mediums include various carbon sources, nitrogen sources and trace elements. The carbon source is exemplified by carbohydrate such as glucose, sucrose, lactose, fructose, maltose, starch, cellulose; fat such as soybean oil, sunflower oil, castor oil and coconut oil; fatty acid such as palmitic acid, stearic acid, and linoleic acid; alcohol such as glycerol and ethanol; and organic acid such as acetic acid.

One of these compounds or a mixture thereof can be used as a carbon source. The nitrogen source is exemplified by such organic nitrogen source as peptone, yeast extract, gravy, malt extract, corn steep liquor (CSL) and bean flour and such inorganic nitrogen source as urea, ammonium sulfate, ammonium chloride, ammonium phosphate, ammonium carbonate and ammonium nitrate. One of these compounds or a mixture thereof can be used as a nitrogen source.

The medium herein can additionally include potassium di-hydrogen phosphate, di-potassium hydrogen phosphate and corresponding sodium-containing salts as a phosphate source. The medium also can include a metal salt such as magnesium sulfate or iron sulfate. In addition, amino acids, vitamins and proper precursors can be added as well. The mediums or the precursors can be added to the culture by batch-type or continuously.

pH of the culture can be adjusted during the cultivation by adding in the proper way such a compound as ammonium hydroxide, potassium hydroxide, ammonia, phosphoric acid and sulfuric acid. To maintain aerobic condition of the culture, oxygen or oxygen-containing gas (e.g. air) can be injected into the culture. The temperature of the culture is conventionally in the range 20° C. to 45° C., preferably in the range 25° C. to 40° C.

The period of cultivation can be continued until the production of L-methionine precursor reaches a wanted level, and the preferable cultivation time is within the range 10 hours to 160 hours.

The method of the invention enables the selective production of L-methionine, which is superior to the conventional chemical synthesis producing D-methionine and L-methionine together, and the production of organic acid such as succinic acid or acetic acid as a by-product without additional independent processes.

The following examples illustrate the present invention without any intention to limit the scope of the present invention which is defined in the annexed claims. Practical and presently preferred embodiments of the present invention are shown in the following examples as illustrative purpose only.

However, it will be appreciated that those skilled in the art, on consideration of this disclosure, may make modifications and improvements within the spirit and scope of the present invention.

Examples 1 to 4

Examples 1 to 4 are carried out with various methyl mercaptan ($CH_3SH$) partial pressures above the reaction medium. These partial pressures range from 10 kPa to 200 kPa in the following examples.

All tests are carried out in an apparatus comprising a 5 L stainless steel jacketed reactor equipped with a stirrer ending with an anchor-paddle and fitted with a stirrer motor with a tachometer, a thermostatically regulated bath allowing for the circulation of oil within the jacket, a thermometric probe in a sheath, a pH probe, a manometer, an inlet for introducing nitrogen and an inlet for introducing methyl mercaptan via a dip-tube. The flow rate of methyl mercaptan is measured and controlled with a mass flow-meter.

The following procedure has been applied for all experiments:

225 g of O-acetyl homoserine (OAHS, 1.4 mol) diluted in 3 L of distilled water are introduced in the reactor.

The reaction medium in heated at 33° C. (reaction temperature) with a stirring velocity set to 600 RPM.

When the reaction temperature reaches 33° C., pH is adjusted at 6.5 adding ammonia at 28 wt % in distilled water.

3 mL of a pyridoxal-5'-phosphate (PLP) solution at 10 mM in distilled water are added in the reactor. PLP is used as coenzyme. The reactor is then hermetically closed.

Beside, methyl mercaptan is liquefied in a pressurized cylinder equipped with a dip tube. A nitrogen pressure higher than the $CH_3SH$ pressure is applied over the liquified $CH_3SH$. By this way, liquid $CH_3SH$ can be introduced in the main reactor into the reaction medium. $CH_3SH$ is spontaneously vaporized in the main reactor.

While stirring, an equilibrium state between the liquid and the gaseous phase in the reactor is reached after a few minutes to one or two hours. The $CH_3SH$ partial pressure is indicated on the manometer and controlled using a valve at the required value for the example. Methyl mercaptan is also introduced with a controlled flow rate.

The methyl mercaptan partial pressure is set to 10 kPa (Example 1), 100 kPa (Example 2), 150 kPa (Example 3), and 200 kPa (Example 4).

9 g of enzyme, such as described in WO 2008/013432, are dissolved in 150 mL distilled water and introduced in the reactor using an intermediate nitrogen pressurized vessel.

The introduction of methyl mercaptan ($CH_3SH$) is stopped when the stoichiometric amount has been introduced (67.2 g, 1.4 mol). From this point, the $CH_3SH$ partial pressure decreases until the end of the reaction time.

All along the reaction time, pH is maintained between 6.2 and 6.5 adding ammonia, as stated hereinbefore. Indeed pH of the reaction medium decreases with time due to the release of acetic acid, which is the co-product of the reaction.

Each hour, a sample is taken out of the reactor and analysed by HPLC (High Pressure Liquid Chromatography) to determine the residual OAHS and the L-Methionine contents.

The following Table 1 collates the results of Examples 1-4:

TABLE 1

| | $CH_3SH$ partial pressure (kPa) | OAHS conversion % | | |
|---|---|---|---|---|
| | | after 1 hour | after 2 hours | after 3 hours |
| Example 1 | 10 | 11.4 | 28.5 | 44.3 |
| Example 2 | 100 | 32.5 | 52.3 | 61.6 |
| Example 3 | 150 | 26.9 | 49.8 | 59.1 |
| Example 4 | 200 | 25.5 | 30.7 | 32.9 |

These results first show the beneficial effect of the $CH_3SH$ partial pressure increase, comparing for example the OAHS conversion rate, i.e. the L-methionine yield, at 3 h in Example 1 and Example 2. A further increase of the $CH_3SH$ partial pressure results in a detrimental effect, see for example the OAHS conversion rate, i.e. the L-methionine yield, at 3 h in Example 4.

These first 4 experiments clearly state that the optimum OAHS conversion rate, and consequently the optimum L-methionine production yield, is reached for a precise $CH_3SH$ partial pressure within the reactor (between 10 kPa and 150 kPa in the above Examples, and preferably between 100 kPa and 150 kPa).

Examples 5 to 7

The tests described in the following Examples 5 to 7 are carried out in a 30 L reactor using the same procedure as described in the previous Examples, however performed at a reaction temperature of 37° C., instead of 33° C., and using another sample of fresh enzyme solution in which the PLP was first solubilized and slowly stirred twenty minutes before the introduction in the reactor.

This enzyme/PLP solution is prepared with 1.2 L of a freshly prepared enzyme solution according to WO 2008/013432 and 25 mL of a 10 mM PLP solution in distilled water. The amount of OAHS used is 1480 g diluted in 18.5 L of distilled water.

The pH of the reaction medium is adjusted to 6.2 with ammonia, as described in the previous examples, and the stirring velocity is set to 300 RPM.

The following table 2 collates the results of examples 5 to 7:

TABLE 2

| | $CH_3SH$ partial pressure (kPa) | OAHS conversion % | | | |
|---|---|---|---|---|---|
| | | after 0.5 hours | after 1 hour | after 2 hours | after 3 hours |
| Example 5 | 10 | 33 | 60 | 92 | 100 |
| Example 6 | 100 | 82 | 97 | 100 | 100 |
| Example 7 | 200 | 65 | 75 | 87 | 87 |

These examples show the same phenomenon regarding the effect of the methyl mercaptan partial pressure. There is a confirmation that for this reaction, there exists an optimum of pressure for which the best performances can be obtained. This optimum $CH_3SH$ partial pressure is here again observed to be between 10 kPa and less than 200 kPa.

The invention claimed is:

1. A process comprising enzymatic converting of an L-methionine precursor with methyl mercaptan in a reaction vessel to obtain L-methionine, wherein the methyl mercaptan partial pressure in the reaction vessel over the reaction medium ranges from 10 kPA to 180 kPA, at the reaction temperature, and wherein the enzyme used for the enzymatic converting is cystathionine-γ-synthase or O-acetyl homoserine sulfhydrylase or O-succinyl homoserine sulfhydrylase.

2. Process according to claim 1, wherein the reaction temperature ranges from 20° C. to 45° C.

3. Process according to claim 1, wherein the L-methionine precursor is chosen from among O-succinyl homoserine (OSHS) and O-acetyl homoserine (OAHS).

4. Process according to claim 1, wherein the enzyme used for the enzymatic converting is prepared using expression of genes according to biotechnological processes.

5. Process according to claim 1, wherein the enzyme used for the enzymatic converting is obtained from a strain of *Pseudomonas* sp., *Chromobacterium* sp., *Leptospira* sp. or *Hyphomonas* sp..

6. Process according to claim 1, wherein the pH of the reaction is maintained between 6 and 7.

7. Process according to claim 1, wherein a co-enzyme is added, said co-enzyme being pyridoxal-5'-phosphate.

8. Process for the preparation of L-methionine comprising the steps of:
   1) preparing a L-methionine precursor-producing strain and producing a L-methionine precursor by the fermentation of the strain,
   2) converting said L-methionine precursor into L-methionine, according to the enzymatic conversion process of claim 1, and
   3) collecting the obtained L-methionine.

9. Process according to claim 8, wherein said L-methionine precursor-producing strain is a prokaryotic or eukaryotic microorganism strain that is able to accumulate L-methionine precursor.

10. Process according to claim 9, wherein the strain is chosen from the group consisting of: *Escherichia* sp., *Erwinia* sp., *Serratia* sp., *Providencia* sp., *Coryne* bacteria sp., *Pseudomonas* sp., *Leptospira* sp., *Salmonellar* sp., *Brevibacteria* sp., *Hypomononas* sp., *Chromobacterium* sp. and *Norcardia* sp. microorganisms; fungi; and yeasts.

11. Process according to claim 9, wherein the strain is obtained in a culture medium that includes various carbon sources, nitrogen sources and trace elements.

12. Process according to claim 11, wherein the carbon source is chosen from the group consisting of: glucose, sucrose, lactose, fructose, maltose, starch, and cellulose; fats; fatty acids; organic acids; and mixtures thereof.

13. Process according to claim 1, wherein the methyl mercaptan partial pressure ranges from 80 kPa to about 160 kPa, at the reaction temperature.

14. Process according to claim 1, wherein the methyl mercaptan partial pressure ranges from 100 kPa to 150 kPa, at the reaction temperature.

15. Process according to claim 1, wherein the reaction temperature ranges from 30° C. to 40° C.

16. Process according to claim 1, wherein the L-methionine precursor is O-acetyl homoserine (OAHS).

17. Process according to claim 1, wherein the methyl mercaptan partial pressure ranges from 100 kPa to 180 kPa, at the reaction temperature.

18. Process according to claim 1, wherein the methyl mercaptan partial pressure ranges from 10 kPa to 150 kPa, at the reaction temperature.

* * * * *